United States Patent [19]

Inoue et al.

[11] Patent Number: 4,667,048

[45] Date of Patent: May 19, 1987

[54] PROCESS FOR DISPROPORTIONATING SILANES

[75] Inventors: Kaoru Inoue; Hiroharu Miyagawa; Masayoshi Itoh, all of Yokohama; Tomohiro Abe, Yokosuka; Kyogo Koizumi, Yokohama; Noriyuki Yanagawa, Hatano, all of Japan

[73] Assignee: Mitsui Toatsu Chemicals, Inc., Tokyo, Japan

[21] Appl. No.: 871,807

[22] Filed: Jun. 9, 1986

[30] Foreign Application Priority Data

Jun. 11, 1985 [JP] Japan ............................ 60-125127

[51] Int. Cl.⁴ .............................................. C07F 7/08
[52] U.S. Cl. .................................................. 556/469
[58] Field of Search ........................................ 556/469

[56] References Cited

U.S. PATENT DOCUMENTS

| | | | |
|---|---|---|---|
| 2,627,451 | 2/1953 | Erickson et al. | 556/469 X |
| 2,723,984 | 11/1955 | Bailey | 556/469 |
| 2,834,648 | 5/1958 | Bailey et al. | 556/469 X |
| 3,322,511 | 5/1967 | Weyenberg | 556/469 X |
| 3,346,349 | 10/1967 | Harding et al. | 556/469 |

*Primary Examiner*—Paul F. Shaver
*Attorney, Agent, or Firm*—Fisher, Christen & Sabol

[57] ABSTRACT

A process for disproportionating silanes, which comprises contacting a silane having at least one Si—H bond represented by the general formula $$R_l H_m SiX_{4-(l+m)}$$

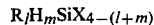

wherein R represents an alkyl or aryl group, X represents a halogen atom or an alkoxy group, l is 0, 1 or 2, and m is 1, 2 or 3 and l+m is 1, 2 or 3, and when l is 2, R's may be identical or different, and when l+m is 1 or 2, X's may be identical or different, with a reaction product of a strong acid-type cation exchange resin with an amine and disproportionating the silane.

13 Claims, No Drawings

PROCESS FOR DISPROPORTIONATING SILANES

BACKGROUND OF THE INVENTION

This invention relates to a process for producing silane compounds such as monosilane or dichlorosilane by disproportionating silanes of the general formula $R_lH_mSiX_{4-(l+m)}$.

With an advance in the electronics industry in recent years, monosilane and chlorosialne have gained increasing importance as materials for the production of polycrystalline silicon, single crystal silicon and amorphous silicon. Monosilane ($SiH_4$) is valuable as a material for producing high-purity silicon, semiconductors for solar cells, epitaxial silicon films, etc., and a great increase in its demand is expected in future. It is desired therefore to develop a process for producing monosilane easily at low cost. On the other hand, chlorosilanes such as dichlorosilane are likewise expected to have a large demand as a material for production of silicon for semiconductors. There is also an expected striking increase in alkylsilanes and alkylhalosilanes as materials for silicones and polycarbosilanes.

Known methods for producing monosilane ($SiH_4$) genrally include the following.

(1) Action of hydrochloric acid on magnesium silicide ($Mg_2Si$).

(2) Action of ammonium chloride or ammonium bromide on magnesium silicide in liquid ammonia.

(3) Reaction of silicon tetrachloride with lithium aluminum hydride in ethers.

(4) Disproportionation or redistribution of trichlorosilane or dichlolrosilane in the presence of a disproportionation catalyst.

(5) Reaction of lithium hydride with silicon tetrachloride in a molten salt composed of lithium chlotetrachloride and potassium chloride (6) Reaction of metallic silicon with hydrogen gas at high temperatures and pressures in the presence of a nickel catalyst In method (1), higher silicon compounds $Si_nH_{2n+2}$ wherein n is an integer of 2 or more are formed as by-products in addition to the monosilane as the desired product. Furthermore, the yield of monosilane is low. Since Mg is expensive, the method is not economical.

Method (2) gives a high yield of monosilane, but is economically disadvantageous since the steps including the separation of ammonia are complex and Mg is expensive.

Method (3) gives highly pure monosilane in a high yield. But its industrial practice is difficult since lithium aluminum hydride used as a reducing agent is expensive and difficulties are encountered in performing the steps continuously.

Method (5) may contribute to a low cost of production because lithium chloride formed as a by-product can be recycled by electrolyzing it to metallic lithium and hydrogenating it. Since, however, this compound is very corrosive and greattly corrodes the equipment, it has not yet gained commercial acceptance.

Method (6) requires high costs for equipment, etc. since it uses a high temperature-pressure reaction. In addition, the decomposition of the product occurs at high temperatures. Hence, this method is not practical.

Method (4) is considered to be advantageous from the standpoint of energy and economy because it involves a catalytic reaction and does not require high temperatures and pressures, and silicon tetrachloride formed as a by-product can be hydrogenated to trichlorosilane and re-used as a material for the disproportionation reaction. This method requires a disproportionation catalyst for chlorosilane. Both homogenous catalysts and solid heterogeneous catalysts are known for disproportionation. Examples of the liquid homogeneous catalysts include tertiary amines (U. S. Pat. No. 2,834,648), cyanamides (U.S. Pat. No. 2,732,280) nitriles (U.S. Pat. No. 2,732,282), α-oxoamines (European Pat. No. 93,640) and inorganic salt/macrocyclic ether catalysts (U.S. Pat. No. 4,548,917). These catalysts, however, are difficult to separate from the products since the catalysts and the resulting silane compounds form a homogeneous phase. Furthermoree, they are not suitable for mass production by a continuous flow reaction. Examples of solid heterogeneous catalysts proposed for gas-solid or liquid-solid heterogeneous reactions include macrocyclic polyether-inorganic salt complexes immobilized with crosslilnked polystyrene (U. S. Pat. No. 4,548,917), and anionic exchange resin catalysts of the tertiary amine type, tertiary amine hydrochloride-type and quaternary ammonium salt type (U.S. Pat. No. 3,968,199 and U.S. Pat. No. 3,928,542). These catalysts are suitable for production of large quantities of monosilane. The macrocyclic ether-type catalysts, however, are very expensive and complex to prepare. The anion exchange resin catalyst are liable to undergo degradation easily since the resins themselves are unstable thermally.

The method (4) is also known for the production of dichlorosilane, but has the same problems as in the production of monosilane. Dichlorosilane is obtained also as a by-product in the production of trichlorosilane from metallic silicon, but its yield is too low to make the method commercially acceptable.

The method (4) is also known for disproportionation reaction of alkylsilanes, but likewise has the aforesaid problems. A method using an aluminum halide as a catalyst is known (U.S. Pat. No. 2,735,861). But the reaction is very slow in the presence of an aluminum halide catalyst, and usually requires temperatures as high as at least 300° C. Moreover, the conversion in this reaction is low.

SUMMARY OF THE INVENTION

It is an object of this invention to provide a process for disproporionating halogenated silanes such as trichlorosilane or hydrocarbon group-containing silanes as a starting materials to produce monosilane or silanes different from the starting silanes.

Another object of this invention is to provide a process for disproportionating silanes in which the reaction is carried out at high temperatures that are advantageous to the formation of the desired silanes from the standpoint of equilibrium of the reaction.

Still another object of this invention is to provide a process for disproportionating silanes using novel catalysts which have higher thermal stability, and therefore enables the reaction to be carried out at higher temperatures stably for a much longer period of time than conventional catalysts.

Yet another object of this invention is to provide a process for disproportionating silanes in the presence of solid heterogeneous catalysts, in which the solid heterogeneous catalyst, the starting silane and the resulting silanes can be easily separated from one another, and the silanes as a disproportionation products can be produced in quantities by a continuous flow re-action.

Other objects of this invention will become apparent from the following description.

These objects of this invention are achieved by a process for disproportionating silanes, which comprises contacting a silane having at least one Si—H bond represented by the general formula

wherein R represents an alkyl or aryl group, X represents a halogen atom or an alkoxy group, l is 0, 1 or 2, and m is 1, 2 or 3 and l+m is 1, 2 or 3, and when l is 2, R's may be identical or different, and when l+m is 1 or 2, X's may be identical or different, with a reaction product of a strong acid-type cation exchange resin with an amine, and disproportionating the silane.

Since the process of this invention uses a novel catalyst which has much higher thermal stability and a longer lifetime than the tertiary amine-type or quaternary ammonium salt-type anion exchange resin catalysts considered to be best among known heterogeneous solid catalysts, the disproportionation reaction of chlorosilanes (such as trichlorosilane) can be carried out stably over a long period of time at high tempratures which are advantageous to the desired composition from the standpoint of the equilibrium of reaction. Moreover, this novel catalyst can be easily prepared.

DETAILED DESCRIPTION OF THE INVENTION

The silane used as a starting material in the process of this invention is a compound having at least one Si—H bond and represented by the following general formula

wherein R represents an alkyl or aryl group, X represents a halogen atom or an alkoxy group, l is 0, 1 or 2, and m is 1, 2 or 3 and l+m is 1, 2 or 3, and when l is 2, R's may be identical or different, and when l+m is 1 or 2, X's may be identical or different.

The alkyl group represented by R preferably has 1 to 10 carbon atoms. Examples of preferred alkyl groups include methyl, ethyl, n-propyl, i-propyl, n-butyl, i-butyl, sec-butyl, t-butyl, n-pentyl, i-pentyl, neopentyl, hexyl, heptyl, vinyl and propenyl groups.

The aryl group for R is preferably has 6 to 20 carbon atoms. Examples of preferred aryl groups include phenyl, o-tolyl, m-tolyl, p-tolyl, 2,3-xylyl, 2,4-xylyl, 2,4,6-mesityl, benzyl and naphthyl groups.

The halogen atom is selected from fluorine, chlorine, bromine and iodine, and chlorine is most preferred.

The alkoxy group preferably has 1 to 10 carbon atoms. Examples of preferred alkoxy groups include methoxy, ethoxy, n-propoxy, i-propoxy, butoxy, pentoxy, phenoxy and benzyloxy groups.

Accordingly, examples of preferred silanes used as the starting material in this invention include trichlorosilane, dichlorosilane, monochlorosilane, monomethyldichlorosilane, monomethylmonochlorosilane, dimethylmonochlorosilane, monoethyldichlorosilane, monoethylmonochlorosilane, diethylmonochlorosilane, mono-npropyldichlorsilane, mono-n-propylmonochlorosilane, di-n-propylmonochlorosilane, mono-phenyldichlorosilane, monophenylmonochlorosilane, monochlorodiphenylsilane, monovinylmonochlorosilane, chloroethoxysilane, dichloroethoxysilane, methylchloroethoxysilane, methylmethoxysilane, methylchloromethoxysilane, dimethylethoxysilane and dimethylmethoxysilane. They may be used singly or in combination.

According to this invention, the reaction product formed between a strong acid-type cation exchange resin and an amine is used as a disproportionation catalyst (to be referred to simply as the catalyst) in the disproportionation of the silane exemplified hereinabove. The reaction product is an adduct obtained by the reaction of the amine with the acidic group of the strong acid-type cation exchange resin, namely the neutralization product. For example, the reaction product between a sulfonic acid type-containing cation exchange resin and an amine is formed by the following reaction of the sulfonic acid group (-SO₃H) with the amine (e.g., NR'₃)

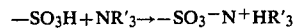

where R' represent, hydrogen, alkyl, etc., and two or three R' atoms or groups may be identical or different.

The important feature of this invention is that the above resin is in the form of an adduct with the amine. Hence, the amine may be any nitrogen-containing compound which can combine with the acidic groups, particularly sulfonic acid groups, of the resin. The formation of the reaction product between the resin and the amine can be confirmed by the fact that when the amine adduct of the cation exchange resin is repeatedly washed with a solvent for the amine or dried under reduced pressure at the boiling point of the amine (more accurately, the boiling point at the pressure employed), no substantial decrease is observed in the weight of the adduct.

The reaction product between a sulfonic acid group-containing cation exchange resin (to be referred to simply as the cation exchange resin), a typical example of the strong acid-type cation exchange resin, and the amine can be prepared, for example, by the following procedure.

Desirably, the resin is first dehydrated by washing with an alcohol and then with benzene, toluene or the like (the resin may occasionally contain as large as 60% or more water). For this purpose, any dehydration method which can effectively dehydrate the resin can be used in this invention. Then, the dehydrated resin is brought into contact with the amine to react them with each other, for example, by the following methods.

(1) A method which comprises reacting a liquid amine directly with the cation exchange resin, preferably with stirring, at a temperature of about 0° to 100° C., preferably at room temperature, washing the reaction product with an inert solvent, and then drying the product at a temperature of about 60° to 70° C. under reduced pressure to remove the excess of the amine.

(2) A method which comprises dissolving a liquid or solid amine in an inert solvent, reacting the amine with the resin, preferably with stirring, at a temperature of about 0° to 100° C., preferably at room temperature, thoroughly washing the product with an inert solvent to remove the excess of the amine, and thereafter drying the product under reduced pressure at about 60° to 70° C.

(3) A method which comprises introducing a gaseous amine (including ammonia) directly into a vessel containing the resin, stirring the mixture and reacting it at a temperature of about 0° to 100° C., preferably at room temperature, and removing rhe excess of the amine under reduced pressure.

(4) A method which comprises introducing a gaseous amine into a suspension of the resin in an inert solvent, reacting them at a temperature of about 0° to 100° C., preferably at room temperature, and thereafter removing the amine and the solvent.

Dehydration may be carried out after the reaction of the amine with the cation exchange resin. For complete proceeding of the reaction, it is preferred that the amount of the amine used be in excess of the equivalent weight in view of the exchange capacity of the cation exchange resin, and after the reaction, the excess of the amine be removed as stated above. The reaction is substantially a neutralization reaction, and ends within a very short period of time. Usually, a reaction time of several minute to several tens of minute suffices.

The amine adduct of the strong acid-type cationic exchange resin obtained as above shows no substantial decrease in weight even when washed repeatedly with a solvent for the amine or dried under reduced pressure at the boiling point of the amine.

The strong acid-type cation exchange resin used in this invention is typically a cation exchange resin having sulfonic acid groups ($-SO_3H$). Examples of the cation exchange resin that can be preferably used in this invention include cation exchange resins manufactured by Rohm & Haas Co. and sold under the tradenames Amberlite IR-116, IR-118, IR-120B, IR-122, IR-124, IR-252 and Amberlyst 15, and sulfonic acid-type products thereof obtained by acid treatment; sulfonic acid-type cation exchange resins manufactured by Bayer AG and sold under the tradenames Lewatit SPC-118, SPC-106, SC-108, SC-104, and SC-102; cation exchange resins manufactured by Mitsubishi Chemical Industries, Ltd. and sold under the tradenames Diaion SK-lA, SK-112 and PK-216; and cation exchange resins manufactured by E. I. du Pont de Nemours & Co. and sold under the tradenames Nafion 501 and Nafion 511.

It is critical in the process of this invention to use the strong acid-type cationic exchange resin. The use of a carboxylic acid-type cation exchange resin cannot lead to the achievement of the object of this invention as will be shown later in Comparative Examples.

The amine used to react with the strong acidtype cation exchange resin may be any nitrogen-containing compound capable of combining with the sulfonic acid groups of the cationic exchange resin as stated above. Examples of the amine that can be used preferably in this invention are shown below.

(a) Hydrogenated nitrogen compounds such as ammonia hydrazine and hydrazine derivatives.

(b) Aliphatic, aromatic or alicyclic amines which are primary, secondary or tertiary, and they are mono- or poly-amines.

(c) Cyclic mono- or poly-amines containing a condensed ring in which at least one nitrogen atom is included in the ring skeleton.

(d) Oxygen-containing amines such as amino acids, amides, aminoalcohols, aminoethers, imides and lactams.

(e) Hetero atom-containing amines which contain hetero atoms such as 0, S and Se.

The secondary or tertiary amines may have identical or different substituents for N.

Specific examples of the hydrogenated nitrogen compounds are substituted hydrazines such as N-methylhydrazine, N-phenylhydrazine, N,N'-dimethylhydrazine and N,N-dimethylhydrazine in addition to ammonia and hydrazine.

Specific examples of the primary amines include monomethylamine, monoethylamine, monopropylamines, monobutylamines, monopentylamines, monohexylamines, monoheptylamines, vinylamine, allylamine, butenylamines, pentenylamines, hexenylamines, pentadienylamines, hexadienylamines, cyclopentylamine, cyclohexylamine, cyclooctylamine, p-menthylamine, cyclopentenylamines, cyclohexenylamines, cyclohexadienylamines, aniline, benzylamine, naphthylamines, naphthylmethylamine, toluidine, tolylenediamines, anisoles, ethylenediamine, ethylenetriamine, monoethanolamine, aminothiophene, glycine, alanine, phenylalanine and aminoacetone.

Specific examples of the secondary amines include dimethylamine, diethylamine, dipropylamines, dibutylamines, dipentylamines, dihexylamines, methylethylamine, methylpropylamines, methylbutylamines, methylpentylamines, methylhexylamines, ethylpropylamines, ethylbutylamines, ethylpentylamines, propylbutylamines, propylpentylamines, propylhexylamines, butylpentylamines, pentylhexylamines, divinylamine, diallylamines, dibutenylamines, dipentenylamines, dihexenylamines, methylvinylamine, methylallylamine, methylbutenylamines, methylpentenylamines, methylhexenylamines, ethylvinylamine, ethylallylamine, ethylbutenylamine, ethylpentenylamines, ethylhexenylamines, propylvinylamines, propylallylamines, propylbutenylamines, propylpentenylamines, propylhexenylamines, butylvinylamines, butylallylamines, butylbutenylamines, butylpentenylamines, butylhexenylamines, vinylallylamine, vinylbutenylamines, vinylpentenylamines, vinylhexenylamines, allylbutenylamines, allylpentenylamines, allylhexenylamines, butenylpentenylamines, butenylhexenylamines, dicyclopentylamine, dicyclohexylamine, methylcyclopentylamine, methylcyclohexylamine, methylcyclooctylamine, ethylcyclopentylamine, ethylcyclohexylamine, ethylcyclooctylamine, propylcyclopentylamines, propylcyclohexylamines, butylcyclopentylamines, butylcyclohexylamines, hexylcyclopentylamines, hexylcyclohexylamines, hexylcyclooctylamines, vinylcyclopentylamine, vinylcyclohexylamine, vinylcyclooctylamine, allylcyclopentylamine, allylcyclohexylamine, allylcyclooctylamine, butenylcyclopentylamines, butenylcyclohexylamines, butenylcyclooctylamines, dicyclopentenylamines, dicyclohexenylamines, dicyclooctenylamines, methylcyclopentenylamines, methylcyclohexenylamines, methylcyclooctenylamines, ethylcyclopentenylamines, ethylcyclohexenylamines, ethylcyclooctenylamines, propylcyclopentenylamines, propylcyclohexenylamines, butylcyclopentenylamines, butylcyclohexenylamines, vinylcyclopentenylamines, vinylcyclohexenylamines, vinylcyclooctenylamines, allylcyclopentenylamines, allylcyclohexenylamines, butenylcyclopentenylamines, butenylcyclohexenylamines, dicyclopentadienylamine, dicyclohexadienylamines, dicyclooctadienylamines, methylcyclopentadienylamine, methyloctadienylamines, cyclohexadienylamines, ethylcylopentadienylamine, ethylcyclohexadienylamines, propylcyclopentadienylamines, propylcyclohexadienylamines, dicyclooctatrienylamines, methylcyclooctatrienylamines, ethylcyclooctatrienylamines, vinylcylopentadienylamine, vinylcyclohexadienylamines, allylcyclopentadienylamine, allylcyclohexadienylamines, diphenylamine, ditolylamines, dibenzylamine, dinaphthylamines, N-methylaniline, N-ethylaniline, N-propylanilines, N-butylanilines, N-methyltoluidines, N-ethyltoluidines, N-propyltoluidines, N-butyltoluidines, N-methylbenzylamine, N-ethylbenzylamine, N-propylbenzylamines, N-butylbenzylamines, N-methylnaphthylamines, N-ethylnaphthylamines, N-propylnaphthylamines, N-vinylaniline, N-allylaniline, N-vinylbenzylamine, N-allylbenzylamine, N-vinyltoluidines, N-allyltoluidines, phenylcyclopentylamine, phenylcyclohexylamine, phenylcyclooctylamine, phenylcyclopentenylamines, phenylcyclohexenylamines, phenylcyclopentadienylamine, N-methylanisoles, N-ethylanisoles, N-vinylanisoles, N-allylanisoles, N-methylethylenediamine, N,N'-dimethylethylenediamine, N-ethylethylenediamine, N,N'-diethylethylenediamine, N,N'-dimethyltolylenediamines, N,N'-diethyltolylenediamines, N-methylethylenetriamine, N,N'-dimethylethylenetriamine, pyrrole, pyrrolidine, imidazole, piperidine, piperazine, methylpyrroles, methylpyrrolidines, methylimidazoles, methylpiperidines, methylpiperazines, ethylpyrroles, ethylpyrrolidines, ethylimidazoles, ethylpiperidines, ethylpiperazines, phthalimide, maleimide, caprolactam, pyrrolidone, morpholine, N-methylglycine, N-ethylglycine, N-methylalanine, N-ethylalanine, N-methylaminothiophenene, N-ethylaminothiophene, 2,5piperazinedione, N-methylethanolamine, N-ethylethanolamine and purine.

Specific examples of the tertiary amines include trimethylamine, triethylamine, tripropylamines, tributylamines, tripentylamines, triheylamines, dimethylethylamine, dimethylpropylamines, dimethylbutylamines, dimethylpentylamines, dimethylhexylamines, diethylpropylamines, diethylbutylamines, diethylpentylamines, diethylhexylamines, dipropylbutylamines, dipropylpentylamines, dipropylhexylamines, dibutylpentylamines, dibutylhexylamines, dipentylhexyllamines, methyldiethylamine, methyldipropylamines, methyldibutylamines, methyldipentylamines, methyldihexyalmines, ethyldipropylamines, ethyldibutylamines, ethyldipentylamines, ethyldihexylamines, propyldibutylamines, propyldipentylamines, propyldihexylamines, butyldipentylamines, butyldihexylamines, pentyldihexylamines, methylethylpropylamines, methylethylbutylamines, methylethylhexylamines, methylpropylbutylamines, methylpropylhexylamines, ethylpropylbutylamines, ethylbutylpentylamines, ethylbutylhexylamines, propylbutylpentylamines, propylbutylhexylamines, butylpentylhexylamines, triviylamine, triallylamine, tributenylamines, tripentenylamines, trihexenylamines, dimethylvinylamine, dimethylallylamine, dimethylbutenylamines, dimethylpentenylamines, diethylvinylamine, diethylallylamine, diethylbutenylamines, diethylpentenylamines, diethylhexenylamines, dipropylvinylamines, dipropylallylamines, dipropylbutenylamines, methyldivinylamine, methyldiallylamine, methyldibutenylamines, ethyldivinylamine, ethyldiallylamine, tricyclopentylamine, tricyclohexylamine, tricyclooctylamine, tricyclopentenylamines, tricyclohexenylamines, tricyclopentadienylamine, tricyclohexadienylamines, dimethylcyclopentylamine, diethylcyclopentylamine, dipropycyclopentylamines, dibutylcyclopentylamines, dimethylcyclohexylamine, diethylcyclohexylamine, dipropylcyclohexylamines, dimethylcyclopentenylamines, diethylcyclopentenylamines, dipropylcyclopentenylamines, dimethylcyclohexenylamines, diethylcyclohexenylamines, dipropylcyclohexenylamines, methyldicylopentenylamine, ethyldicylopentenylamine, propylcyclopentenylamines, methyldicyclohexylamine, ethyldicylclohexylamine, propylcyclodicyclohexylamine, hexylamines, methyldicyclopentenylamines, ethyldicyclopentenylamines, propyldicyclopentenylamines, N,N-dimethylaniline, N,N-dimethylbenzylamine, N,N-dimethyltoluidines, N,N-dimethylnaphthylamines, N,N-diethylaniline, N,N-diethylbenzylamine, N,N-diethyltoluidines, N,N-diethylnaphthylamines, N,N-dipropylanilines, N,N-dipropylbenzylamines, N,N-dipropyltoluidines, N,N-dipropylnaphthylamines, N,N-divinylaniline, N,N-diallylaniline, N,N-divinyltoluidines, N,N-diallylaniline, diphenylmethylamine, diphenylethylamine, diphenylpropylamines, dibenzylmethylamine, dibenzylethylamine, dibenzylcyclohexylamine, dibenzylvinylamine, dibenzylallylamine, ditolylmethylamines, ditolylethylamines, ditricyclohexylamines, ditolylvinylamines, triphenylamine, tribenzylamine, tri(tolyl)amines, trinaphthylamines, N,N,N',N'tetramethylethylenediamine, N,N,N',N'-tetraethylethylenediamine, N,N,N',N'-tetramethyltolylenediamines, N,N,N',N'-tetraethyltolylenediamines, N-methylpyrrole, N-methylpyrrolidine, N-methylimidazole, N,N''-dimethylpiperazine, N-methylpiperidine, N-ethylpyrrole, N-methylpyrrolidine, N-ethylimidazole, N,N'-diethylpiperazine, N-ethylpiperidine, pyridine, pyridazine, pyrazine, quinolines, quinazoline, quinacridine, N-methylpyrrolidone, N-methylmorpholine, N-ethylpyrrolidone, N-ethylmorpholine, N,N-dimethylanisole, N,N-diethylanisoles, N,N-dimethylglycine, N,N-diethylglycine, N,N-dimethylalanine, N,N-diethylalanine, N,N-dimethylethanolamine, and N,N-di- methylaminothiophene.

It is apparent from the foregoing statement that the amines used in this invention are compounds having an aliphatic or alicyclic saturated or unsaturated hydrocarbon group, an aromatic hydrocarbon group, an oxygen- and/or sulfur- and/or selenium-containing hydrocarbon group, etc. bonded to at least one nitrogen atom.

In the present invention, the starting silane is disproportionated by bringing it into contact with the reaction product of the strong acid-type cation exchange resin and the amine, for example the sulfonic acid salt-type ammonium, as the catalyst.

Generally, the disproportionation reaction in this invention is a reaction of forming from the starting silane, $(R_lH_mSiX_{4-(l+m)})$, a silane having more hydrogen atoms and less halogen atoms or alkoxy groups and a silane having less hydrogen atoms and more halogen atoms or alkoxy groups as schematically shown below.

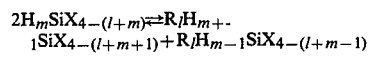

For example, when the starting silane is trichlorosilane ($l=0$, $m=1$ and $X=Cl$ in general formula $R_lH_mSiX_{4-(l+m)}$), the disproportionation reaction is expressed by the following formulae.

$$2SiHCl_3 \rightleftarrows SiH_2Cl_2 + SiCl_4 \quad \text{(III)}$$

$$2SiH_2Cl_2 \rightleftarrows SiH_3Cl + SiHCl_3 \quad \text{(IV)}$$

$$2SiH_3Cl \rightleftarrows SiH_4 + SiH_2Cl_2 \quad \text{(V)}$$

The disproportionation is an equilibrium reaction, and by removing at least one of the resulting disproportionated silane compounds by such means as distillation, the reaction can be caused to proceed continuously in the right direction. The desired silane may be easily separated from the resulting disproprotionated silane mixture by such means as distillation.

When the catalyst of this invention is used, the rate of the disproportionation reaction is very high, and an equilibrium is reached within a short period of time, for example after a contact time of several seconds in the case of carrying out the reaction in the vapor phase. From the standpoint of the equilibrium composition of the reaction mixture, the temperature is desirably as high as possible within the range in which the stability of the product and the catalyst can be maintained. In view of this and of thermal energy, the reaction temperature in the disporportionation (or redistribution) in this invention is in the range of 0° to 350° C., preferably 50° to 150° C. At these temperatures, the reaction can be carried out at sufficiently high conversions. By using the catalyst of this invention and properly selecting the kind of the starting material, a reaction reverse to the above disproportionation reaction can be easily performed. For example, dichlorosilane may be easily obtained from monosilane and silicon tetrachloride.

The disproportionation in accordance with this invention can basically be carried out in the vapor-solid phase or liquid-solid phase under atmospheric, superatmospheric or subatmospheric pressures. For example, the following procedures (1), (2) and (3) may be employed because they are easy to practice.

(1) The catalyst and the starting silane are put into a reaction vessel, and heated under atmospheric pressure with stirring under reflux.

(2) The catalyst and the starting silane are put into an autoclave, and heated under pressure with stirring.

(3) The catalyst is filled in a single tubular reactor, and the liquid or gaseous starting silane is introduced continuously into the catalyst layer under atmospheric superatmospheric or subatmospheric pressures to react the silane (in this procedure, a diluent, for example an inert solvent such as benzene or chlorobenzene or an inert gas may be used to control the rate of the reaction).

To treat a large amount of the silane, a continuous method based on the procedure (3) is preferably used. The invention however should not be construed to be limited to these procedures alone.

The starting silanes used in this reaction and the resulting silanes such as monosilane and halosilanes are active and easily decompose upon contact with water, alcohols, and aqueous alkaline solutions. Some of them react vigorously with oxygen and decompose with flaming. For this reason, the reaction should be carried out in an atmosphere inert to the starting silanes and the produced silanes. For example, the disproportionation reaction is carried out preferably after the reaction system is first maintained in an atmosphere of an inert gas, such as hydrogen, nitrogen, helium or argon, thoroughly dehydrated, dried and deoxygenated.

EXAMPLES

The following examples illustrate the present invention specifically.

In Examples 1 to 6, the product was analyzed in the gaseous state after the outlet of the reactor was heated to 70° C. and the product was introduced as a uniform gas kept at this temperature into a constanttemperature sampler for gas chromatography.

In Examples 7 and 8, the gas and the reaction solution were sampled respectively, and anlayzed by gas chromatography.

Preparation of catalysts (a) Dehydration of Amberlyst 15 and Lewatit SPC-118

Each of the resins was first immersed in ethanol, followed by stirring and decantation. This procedure was repeated five times, and then the resin was collected by filtration. The resin was then washed three times with ethanol dried by molecular sieve 3A, and washed likewise with toluene five times. The washed resin was dried at 60° to 70° C. under reduced pressure for 4 hours. The resins had a water content of less than 0.5%.

(b) Preparation of reaction catalysts (b-1) Amberlyst-15/triethylamine catalyst (catalyst 1) and Amberlyst-15/pyridine catalyst (catalyst 2)

Dried Amberlyst-15 (10 g), 20 ml of n-heptane and 20 ml of triethylamine or pyridine were mixed and stirred at room temperature for 3 hours to complete the netralization reaction. The solid was separated by filtration, washed with n-heptane, and dried at 60° to 70° C. for 5 hours.

(b-2) Amberlyst-15/N-methylpyrrolidone catalyst (catalyst 3)

Dried Amberlyst (10 g), 20 ml of toluene and 20 ml of N-methylpyrrolidone were heated with stirring at 50° to 60° C. for 3 hours. The solid was separated by filtration, washed with toluene, and dried at 60° to 70° C. under reduced pressure for 5 hours.

(b-3) Amberlyst-15/ammonia catalyst (catalyst 4)

Ammonia gas was introduced for 5 hours at a flow rate of 40 ml/min. into 10 g of dried Amberlyst and 20 ml of n-heptane with stirring. Then, with stirring, the excess of ammonia was driven off at 50° to 60° C. The solid was separated by filtration, and dried at 60° to 70° C. under reduce pressure for 5 hours.

(b-4) Lewatit SPC-118/triethylamine catalyst (catalyst 5) and Lewatit SPC-118/aniline catalyst (catalyst 6)

Dried Lewatit SPC-118 was reacted with triethylamine or aniline in the same way as in (b-2) above. The solid product was separated by filtration and dried.

(b-5) Lewatit SPC-118/tri-n-butylamine catalsyt (catalyst 7)

Dried Lewatit SPC-118 was reacted with tri-n-butylamine in the same way as in (b-2). The solid product was separated by filtration and dried.

The weight increases and exchange capacities of the resins led to the determination that in catalysts 1 to 7, almost all sulfonic acid groups reacted with the amines.

EXAMPLE 1

Each of catalysts 1 to 7 was filled in a Pyrex glass tube having an inside diameter of 11 mm in an amount of 50 mm (filled volume 4.75 ml), and the glass tube was heated to 100° C. in an oil bath. Trichlorosilane (purity 99.9%) was fed into the glass tube at a rate of 25 g/hr, and passed through the tube for several hours. When the reaction reached a steady state, the reaction gas was analyzed. The results are shown in Table 1.

TABLE 1

| Catalyst | Composition of the product (mole %) | | | |
|---|---|---|---|---|
| | $SiH_3Cl$ | $SiH_2Cl_2$ | $SiHCl_3$ | $SiCl_4$ |
| 1 | 0.8 | 9.6 | 78.5 | 11.1 |
| 2 | 0.7 | 5.7 | 86.9 | 6.6 |
| 3 | 0.6 | 8.3 | 81.7 | 9.4 |
| 4 | — | 2.9 | 93.4 | 3.7 |
| 5 | 1.1 | 10.1 | 76.9 | 11.9 |
| 6 | 0.3 | 4.3 | 89.7 | 5.2 |
| 7 | 0.5 | 11.5 | 75.2 | 12.3 |

The results demonstrate that these catalyst have sufficient activity in the disproportionation reaction of silanes.

EXAMPLE 2

Trichlorosilane was disproportionated in the same way as in Example 1 using catalyst 5 (Lewatit SPC-118/triethylamine) except that the amount of the silane fed and the reaction temperatures were varied as shown in Table 2. The results are shown in Table 2 together with the data obtained in Example 1 for catalyst 5.

The product gas was anlayzed after several hours elapsed from the initiation of the reaction and the reaction reached a fully steady state.

TABLE 2

| No. | Amount of $SiHCl_3$ fed (g/hr) | Reaction temperature (°C.) | Composition of the product (mole %) | | | |
|---|---|---|---|---|---|---|
| | | | $SiH_3Cl$ | $SiH_2Cl_2$ | $SiHCl_3$ | $SiCl_4$ |
| 1 | 25 | 60 | 0.6 | 5.2 | 86.9 | 7.3 |
| 2 | 25 | 80 | 0.9 | 8.3 | 80.9 | 9.9 |
| 3 | 25 | 100 | 1.1 | 10.1 | 76.9 | 11.9 |
| 4 | 25 | 120 | 1.2 | 11.4 | 73.7 | 13.7 |
| 5 | 88 | 120 | 1.0 | 11.6 | 73.8 | 13.6 |

It is seen from Table 2 that in a reaction at 120° C., the product gas suffieintly reached the equilibrium composition even when the amount of the starting trichlorosilane fed was 88 g/hr.

EXAMPLE 3 Various catalysts were prepared as in the above preparation procedure (b-2) from dried Lewatit SPC-118 and the amines indicated in Table 3. Trichlorosilane was disproportionated under the same reaction conditions as in Example 1 using each of the catalysts prepared. After the reaction reached steady state, the product gas was analyzed by gas chromatography. The results are shown in Table 3.

TABLE 3

| No. | Amine | Composition of the product (mole %) | | | |
|---|---|---|---|---|---|
| | | $SiH_3Cl$ | $SiH_2Cl_2$ | $SiHCl_3$ | $SiCl_4$ |
| 1 | diethylamine | 0.7 | 9.4 | 79.2 | 10.7 |
| 2 | di-n-butylamine | 0.6 | 11.8 | 75.7 | 11.9 |
| 3 | ethylenediamine | 0.8 | 10.9 | 76.3 | 12.0 |
| 4 | ethanolamine | 0.4 | 6.0 | 86.7 | 6.9 |
| 5 | pyrrole | 0.3 | 8.2 | 82.5 | 8.9 |
| 6 | piperidine | 0.5 | 7.4 | 84.8 | 7.3 |
| 7 | pyrrolidine | 0.4 | 7.5 | 83.8 | 8.3 |
| 8 | N—methyl-pyrrolidine | 0.3 | 7.6 | 84.0 | 8.1 |
| 9 | morpholine | 0.2 | 6.2 | 87.3 | 6.3 |
| 10 | benzylamine | 0.4 | 4.2 | 90.4 | 5.0 |
| 11 | alpha-naphthylamine | 0.2 | 3.7 | 91.8 | 4.3 |
| 12 | alpha-picoline | 0.7 | 11.0 | 85.3 | 13.0 |
| 13 | thiazole | 0.4 | 9.3 | 79.5 | 10.8 |
| 14 | 2-aminopyridine | 0.5 | 8.1 | 82.4 | 9.0 |
| 15 | DBU (*) | 0.3 | 11.5 | 76.3 | 11.7 |

(*): 1,8-diazabicyclo[5,4,0]-7-undecene

EXAMPLE 4

Dichlorosilane was fed at a rate of 20 g/hr into the same apparatus as used in Example 1 filled with the same amount of the catalyst of Example 2 (catalyst 5) as used in Example 1 to disproportionate dichlorosilane. The results are shown in Table 4.

TABLE 4

| No. | Reaction temperature (°C.) | Composition of the product (mole %) | | | | |
|---|---|---|---|---|---|---|
| | | $SiH_4$ | $SiH_3Cl$ | $SiH_2Cl_2$ | $SiHCl_3$ | $SiCl_4$ |
| 1 | 60 | 8.6 | 14.2 | 45.6 | 31.2 | 0.4 |
| 2 | 80 | 10.3 | 15.7 | 34.9 | 38.4 | 0.7 |
| 3 | 100 | 13.8 | 14.4 | 30.2 | 40.7 | 0.9 |
| 4 | 120 | 15.9 | 13.7 | 26.9 | 42.3 | 1.2 |

The results show that the catalyst 5 has sufficiently high catalytic activity also in the disproportionation reaction of dichlorosilane.

COMPARATIVE EXAMPLE 1

Dried Amberlyst 15 and Lewatit SPC-118 were filled into the same reaction tube as used in Example 1 and trichlorosilane was fed into it at a rate of 25 g/hr at a temperature of 60°, 80°, 100° and 120° C., respectively. With these two types of cation exchange resin, the formation of dichlorosilane and silicon tetrachloride was not observed, and only the trichlorosilane was recovered. The results show that the acid cation exchange resins alone cannot induce disproportionation reaction.

EXAMPLE 5

Trichlorosilane was fed at a rate of 25 g/hr, and reacted as in No. 4 of Example 2 at 120° C. Forty hours after the initiation of the reaction, the reaction product was found to comprise 1.3 mole % of $SiH_3Cl$, 10.2 mole % of $SiH_2Cl_2$, 76.7 mole % of $SiHCl_3$ and 11.9 mole % of $SiCl_4$. No substantial decrease in catalytic activity was observed.

COMPARATIVE EXAMPLE 2

The same apparatus as used in Examples 1 to 3 was filled with the same amount of Amberlyst A-21, and trichlorosilane was introduced into the catalyst layer and reacted under the same conditions as in No. 4 of Example 2. The reaction product was analyzed 1 hour and hours later, respectively. As shown in Table 5, a marked decrease in activity was observed only 40 hours after the initiation of the reaction.

TABLE 5

| Time elapsed (hours) | Composition of the product (mole %) | | | |
|---|---|---|---|---|
| | $SiH_3Cl$ | $SiH_2Cl_2$ | $SiHCl_3$ | $SiCl_4$ |
| 1 | 1.1 | 11.5 | 73.8 | 13.6 |

TABLE 5-continued

| Time elapsed (hours) | Composition of the product (mole %) | | | |
|---|---|---|---|---|
| | SiH$_3$Cl | SiH$_2$Cl$_2$ | SiHCl$_3$ | SiCl$_4$ |
| 40 | — | 7.2 | 85.4 | 7.4 |

COMPARATIVE EXAMPLE 3

Lewatit CNP 80 (a carboxylic acid type cation exchange resin) was reacted with aqueous ammonia at room temperature for 3 hours with stirring (exotherm was observed during neutralization). The resin was well washed with ethanol and then with toluene, and dried under reduced pressure. The resulting ammonia-adduct resin was filled in the same apparatuus as used in Example 1 in the same amount. Trichlorosilane (purity 99.9%) was passed into the catalyst layer at a flow rate of 25 g/hr, and disproportionated at 60° C. and 100° C. respectively. Only the starting trichlorosilane was recovered, and no substantial disproportionation was observed.

COMPARATIVE EXAMPLE 4

Ten grams of the carboxylic acid-type cation exchange resin Lewatit CNP-80, dehydrated and dried as above, and 20 ml of triethylamine were reacted in 40 ml of toluene at room temperature with stirring, and toluene and the excess of the same amine were removed under reduced pressure at 40° to 50° C. The residue was dried until there was no change in weight. The product was used as a catalyst and filled in the same reaction apparatus as used in Example 1 in the same amount. Trichlorosilane was introduced at a flow rate of 325 g/hr, and reacted at 60° C. Only the starting trichlorosilane was recovered, and no substantial disproportionation of the silane was observed.

It is seen from the results of Comparative Examples 3 and 4 that the reaction product of the carboxylic acid-type cation exchange resin and the amine has substantially no appreciable activity in disproportionation.

EXAMPLE 6

Catalyst 7 (Lewatit SPC-118/tri-n-butylamine) was filled into a Pyrex glass tube having an inside diameter of 11 mm in an amount of 50 mm (filled voluem 4.75 ml). Trichlorosilane (purity 99.9%) was introduced into the catalyst layer at a flow rate of 25 g/hr, and reacted at 120° C. for 830 hours, and then again reacted at 100° C. for 30 minutes to reach steady state. The reaction products at 100° C. were analyzed and found to comprise 0.3 mole % of SiH$_3$Cl, 11.0 mole % of SiH$_2$Cl$_2$, 77.0 mole % of SiHCl$_3$ and 11.7 mole % of SiCl$_4$. This shows that even after use for as long as 830 hours at a temperature of as high as 120° C., the catalyst hardly underwent degradation, and maintained high activity.

It is clear from the above data that the catalyst in accordance with this invention has high-temperature thermal stability for a very long period as compared with the anion exchange resin catalyst used in Comparative Example 2.

EXAMPLE 7

A 100 ml autoclave was charged with 5.0 g of the same catalyst as used in Example 5 and 40 g of methyldichlorosilane (CH$_3$SiHCl$_2$), and with gentle stirring, methyldichlorosilane was reacted at 40° C. for 20 hours. The reaction product was analyzed by gas chromatography. As shown by the results given in Table 6, the catalyst had very high activity in disproportionation.

TABLE 6

| CH$_3$SiCl$_3$ | CH$_3$SiHCl$_2$ | CH$_3$SiH$_2$Cl |
|---|---|---|
| 7.2 mole % | 85.9 mole % | 6.9 mole % |

EXAMPLE 8

A 100 ml autoclave was charged with 5.0 g of the same catalyst as used in Example 5, 20.1 g of methyldichlorosilane (CH$_3$SiHCl$_2$) and 13.7 g of trichlorosilane (63.4 mole % of methyldichlorosilane and 36.6 mole % of trichlorosilane). The silanes were reacted at 40° C. for 2.5 hours with gentle stirring. The composition of the product are shown in Table 7.

TABLE 7

| Silane | Mole % |
|---|---|
| SiH$_4$ | 0.8 |
| SiH$_3$Cl | 4.7 |
| CH$_3$SiH$_2$Cl | 1.2 |
| SiH$_2$Cl$_2$ | 15.3 |
| HSiCl$_3$ | 15.4 |
| CH$_3$SiHCl$_2$ | 31.5 |
| SiCl$_4$ | 0.4 |
| CH$_3$SiCl$_3$ | 30.7 |

UTILITY

By using a novel catalyst composed of the reaction product of the strong acid-type cation exchange resin and the amine which has higher heat stability and a longer life than anion exchange resin catalysts which are typical known heterogeneous solid catalysts, the present invention enables the disproportionation reaction of silanes to be carried out stably over a long period of time at high temperatures which are advantageous to the desired composition from the standpoint of equilibrium of reaction. Moreover, the catalyst used in this invention is easy to prepare. Hence, the present invention achieves a great improvement over the conventional heterogenous catalysts which are thermally unstable and should be used at low temperatures and have a low disproportionation ratio. The process of this invention, therefore, is expected to have great utility in industrial practice.

What is claimed is:

1. A process for disproportionating silanes, which comprises contacting a silane having at least one Si-H bond represented by the general formula

wherein R represents an alkyl or aryl group, X represents a halogen atom or an alkoxy group, is 0, 1 or 2, and m is 1, 2 or 3 and +m is 1, 2 or 3, and when is 2, R's may be identical or different, and when +m is 1 or 2, X's may identical or different, with a reaction product of a strong acid-type cation exchange resin with an amine, and disproportionating the silane.

2. The process of claim 1 wherein the strong acid-type cation exchange resin is a sulfonic acid-type cation exchange resin containing sulfonic acid groups.

3. The process of claim 1 wherein the amine is a hydrogenated nitrogen compound.

4. The process of claim 3 wherein the hydrogenated nitrogen compound is ammonia, hydrazine or a hydrazine derivative.

5. The process of claim 1 wherein the amine is an aliphatic, aromatic or alicyclic amine.

6. The process of claim 5 wherein the amine is a primary, secondary or tertiary amine.

7. The process of claim 5 wherein the amine is mono- or poly-amine.

8. The process of claim 1 wherein the amine is a cyclic mono- or poly-amine containing a condensed ring in which at least one nitrogen atom is included in the ring skeleton.

9. The process of claim 1 wherein the amine is an amino acid, an amide, an aminoalcohol, an aminoether, an imide or a lactam.

10. The process of claim 1 wherein the amine is a hetero atom-containing amine.

11. The process of claim 10 wherein the hetero atom is O, S or Se.

12. The process of claim 1 wherein the contacting is carried out at a temperature of 0° to 350° C.

13. The process of claim 12 wherein the contacting is carried out at a temperature of 50° to 150° C.

* * * * *